United States Patent [19]

Krebs

[11] Patent Number: 5,531,218

[45] Date of Patent: Jul. 2, 1996

[54] APPARATUS FOR THE MONITORED METERING OF NO INTO PATIENTS' RESPIRATORY AIR

[75] Inventor: Christian Krebs, Vienna, Austria

[73] Assignee: Messer Griesheim GmbH, Germany

[21] Appl. No.: 226,550

[22] Filed: Apr. 12, 1994

[30] Foreign Application Priority Data

Apr. 17, 1993 [DE] Germany .......................... 43 12 431.3
Jul. 29, 1993 [DE] Germany .......................... 43 25 319.9

[51] Int. Cl.⁶ ............................................... A61M 15/00
[52] U.S. Cl. ............................ 128/203.12; 128/202.22; 128/203.25
[58] Field of Search ..................... 128/200.14, 200.23, 128/203.12, 202.22, 203.25

[56] References Cited

U.S. PATENT DOCUMENTS 5,396,882   3/1995   Zapol ................................ 128/203.12

OTHER PUBLICATIONS

"Inhaled Nitric Oxide: A Selective Pulmonary Vasodilator Reversing Hypoxic Pulmonary Vasoconstriction", by Frostell et al.; Circulation (1991); 83: 2038–2047.

Primary Examiner—Aaron J. Lewis
Attorney, Agent, or Firm—Connolly & Hutz

[57] ABSTRACT

Apparatus for the monitored metering of NO into patients' respiratory air

An apparatus for the monitored metering of NO into the respiratory air of patients with ARDS or similar disorders essentially comprises a respirator (1), an NO metering container (3), a metering unit (4), an analyzer (2) for determining the concentration of NO in the patient's respiratory air and a control unit (6a) which acts on the metering unit. In order for the apparatus to operate fault-free on continuous operation and quickly respond to changes in the NO concentration, a dehumidifier (23) and a measurement gas pump (20) are located in the connecting line between analyzer and respirator. An NO limit monitoring unit (18) which acts on the metering unit and is connected to the analyzer is preferably provided. It is furthermore advantageous for a monitoring and automatic control unit (6b) to be responsible for adjusting the NO to be metered by determining the volumetric flows of respiratory gas and NO on the basis of the analyzed value of NO. FIG. 1.

26 Claims, 2 Drawing Sheets

APPARATUS FOR THE MONITORED METERING OF NO INTO PATIENTS' RESPIRATORY AIR

BACKGROUND OF THE INVENTION

The invention relates to an apparatus for the monitored metering of NO into the respiratory air and analysis of the inspiratory and expiratory air of patients with, for example, ARDS or similar syndromes.

ARDS (adult respiratory distress syndrome) is a serious failure of the lungs of adults in which a persistent serious disturbance of gas exchange in the lungs is accompanied by an elevated blood pressure in the pulmonary circulation. This elevated pressure leads to a serious stress on the right heart and consequently to right heart failure. Apart from ARDS, elevated pressure in the pulmonary circulation may also occur in preterm infants and associated with certain cardiac malformations. It is possible per se to reduce the elevated pressure in the pulmonary circulation by administering agents which lower blood pressure. However, these act on the entire blood circulation. Since, as a rule, the blood pressure is already too low in patients with ARDS, it is therefore possible to administer such agents which lower blood pressure only with great restrictions.

It has been known for some years that a specific reduction in the elevated pressure in the pulmonary circulation is possible by metering NO (nitric oxide) into patients' respiratory air. The NO has a vasodilating effect and, as a consequence of the enlargement of the cross-section of vessels, leads to a reduction in the blood pressure in the pulmonary circulation. The difficulties arising in treatment with NO are that fault-free treatment with NO must be ensured over a period of several weeks. Another difficulty which may arise is that toxic $NO_2$ (nitrogen dioxide) may be formed from part of the NO in the patient's lung.

SUMMARY OF THE INVENTION

The invention is therefore based on the object of producing an apparatus for the monitored metering of NO into patients' respiratory air, which apparatus ensures reliable long-term operation and very quickly reacts to inadmissible changes in the concentration of NO and, where appropriate, $NO_2$ in the patient's respiratory air.

Advantageous further developments of the invention are indicated in the dependent claims.

Analyzers suitable for the apparatus according to the invention operate, for example, on the principle of infrared absorption measurement, the principle of measurement by electrochemical sensors or the chemiluminescence detector principle. The chemiluminescence detector has the advantage that it is possible with it to establish the concentration of NO and $NO_2$ simultaneously.

Since analyzers of these types react very sensitively to moisture, which may lead to unwanted side effects and cessations of operation, according to the invention a dehumidifying device such as, for example, condenser, in which the moisture present in the respiratory gas is removed, for example by condensing out, is located in the measurement gas line leading to the analyzer. This results in fault-free operation of the apparatus over long periods. Furthermore, a measurement gas pump is located in the measurement gas line leading to the analyzer. This extracts from the tube leading from the respirator to the patient an amount of respiratory air which is greater than the analyzer needs per se. The unneeded amount of measurement gas is released to the environment through a bypass line. The result of this is that changes in the concentration of NO and, where appropriate, $NO_2$ can be detected very quickly by the analyzer, and the NO dosage can be altered correspondingly where appropriate.

BRIEF DESCRIPTION OF THE DRAWINGS

Two exemplary embodiments of the invention are to be explained by means of the attached drawings.

DETAILED DESCRIPTION

Identical parts of the apparatus have been provided with identical reference numbers in the figures.

Figure 1:
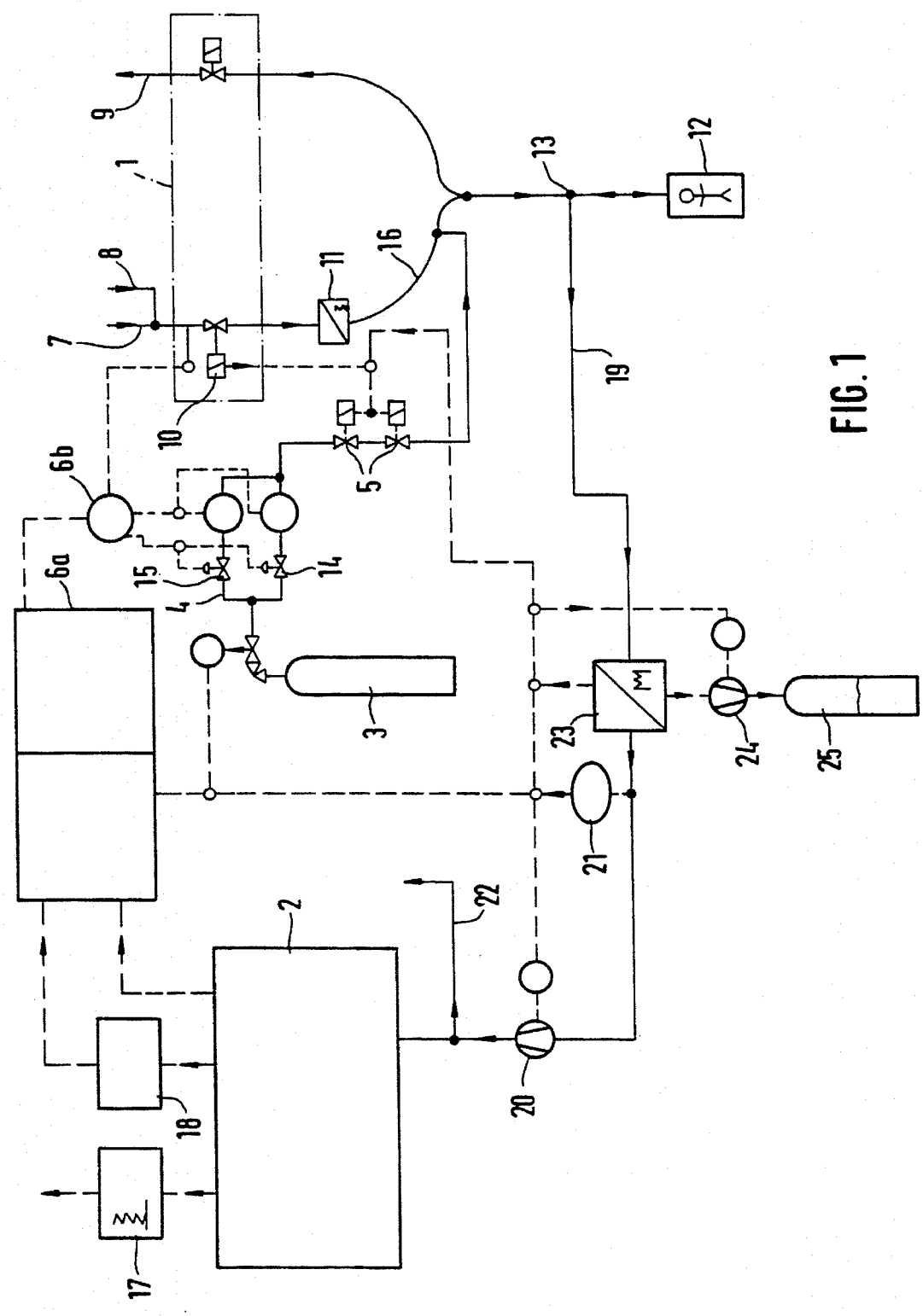
FIG. 1 shows an apparatus which is suitable for any analyzers for determining NO in a patient's respiratory air.

The essential components of the apparatus depicted in FIG. 1 are the respirator 1, the analyzer 2, the NO metering container 3, the metering unit 4 with control valves 14, 15, and the control unit 6a. The open- and closed-loop control connections are depicted in the drawing as broken lines, and the gas lines are shown as full lines. These connections have for the most part not been provided with reference numbers.

The respirator 1 is the actual breathing apparatus. It has connections 7 and 8 for respiratory air and oxygen, and a connector 9 for discharging exhaled air. The oxygen-enriched air flows through the inspiration valve 10 and the humidifier 11. The patient 12 thus receives through tube 13 warm respiratory air which is highly enriched with oxygen and moisture. The NO metering container 3 is a gas cylinder and contains a mixture of NO in $N_2$ 300–3000 vpm. It is connected to the respirator 1, preferably to its respiratory arm or outlet passageway 16. The analyzer 2 measures the NO concentration. The control valves 5 may, inter alia, also be timed by the signal from the inspiration valve 10. If the latter is not available, the control valves 14, 15 adjust to 0 on the basis of the inspiratory volumetric flow and cut off the NO supply. However, the control valves 5 are intended to be safety shutoff valves in the NO supply. Thus, there is analysis of the metered-in NO content not only during the inspiratory phase (inhalation) but of the exhaled gas mixture during the expiratory phase (exhalation). This arrangement therefore makes it possible to interpret the analysis product further and, in particular, to interpret the NO intake correspondingly.

The NO concentration measured in the analyzer 2 is continuously recorded by the recorder 17. The measured concentrations are passed on to the control unit 6a which in turn adjusts, via the metering unit 4 with the control valves 14, 15, the amount of NO supplied to the patient.

The monitoring and automatic control unit 6b calculates, by measuring the volumetric flow of respiratory air and oxygen flowing through the connections 7 and 8 and on the basis of the concentration set on the monitoring and automatic control unit 6b, the required volumetric flow of NO to be metered in. The latter is fixed by the automatic valve adjustment. In place of a control valve it is also possible to use a plurality of valves arranged in parallel for this purpose. The NO volumetric flow measured in the NO metering line is fed back as controlled variable. The monitoring and automatic control unit 6b adjusts, on the basis of the analyzed value of NO, the amount of NO metered in (double-meshed control loop).

This control design makes it possible not only to select a volume-controlled ventilation but also to practice all the other types of ventilation. The NO concentrations are in this case always kept constant. The spontaneous breathing type of ventilation is therefore also conceivable so that it is also possible to ventilate patients not under complete intensive care.

In addition, a limit monitoring unit 18 is located between the analyzer 2 and control unit 6a. The latter switches off the NO supply to the patient if the concentration of NO measured in the respiratory gas in the tube 13 exceeds the maximum of 60 vpm which is hazardous for the patient. However, a limit shift is possible since the limit is designed to be variably adjustable between 0 and 60 vpm. The measurement gas for the analyzer 2 is removed from the tube 13 by the analysis extractor 19. The analysis extractor 19 should be as close as possible to the patient.

A measurement gas pump 20 is provided according to the invention and, in conjunction with a flow monitoring unit 21, extracts from the tube 13 a measurement gas stream which is considerably larger than required for operating the analyzer. The excess amount of measurement gas is discharged through the bypass line 22. This measure according to the invention results in the analyzer 2 very quickly detecting changes in the concentration of NO in the respiratory gas. The NO supply can be adjusted by the control unit 6a and the monitoring and automatic control unit 6b correspondingly quickly.

Figure 2:
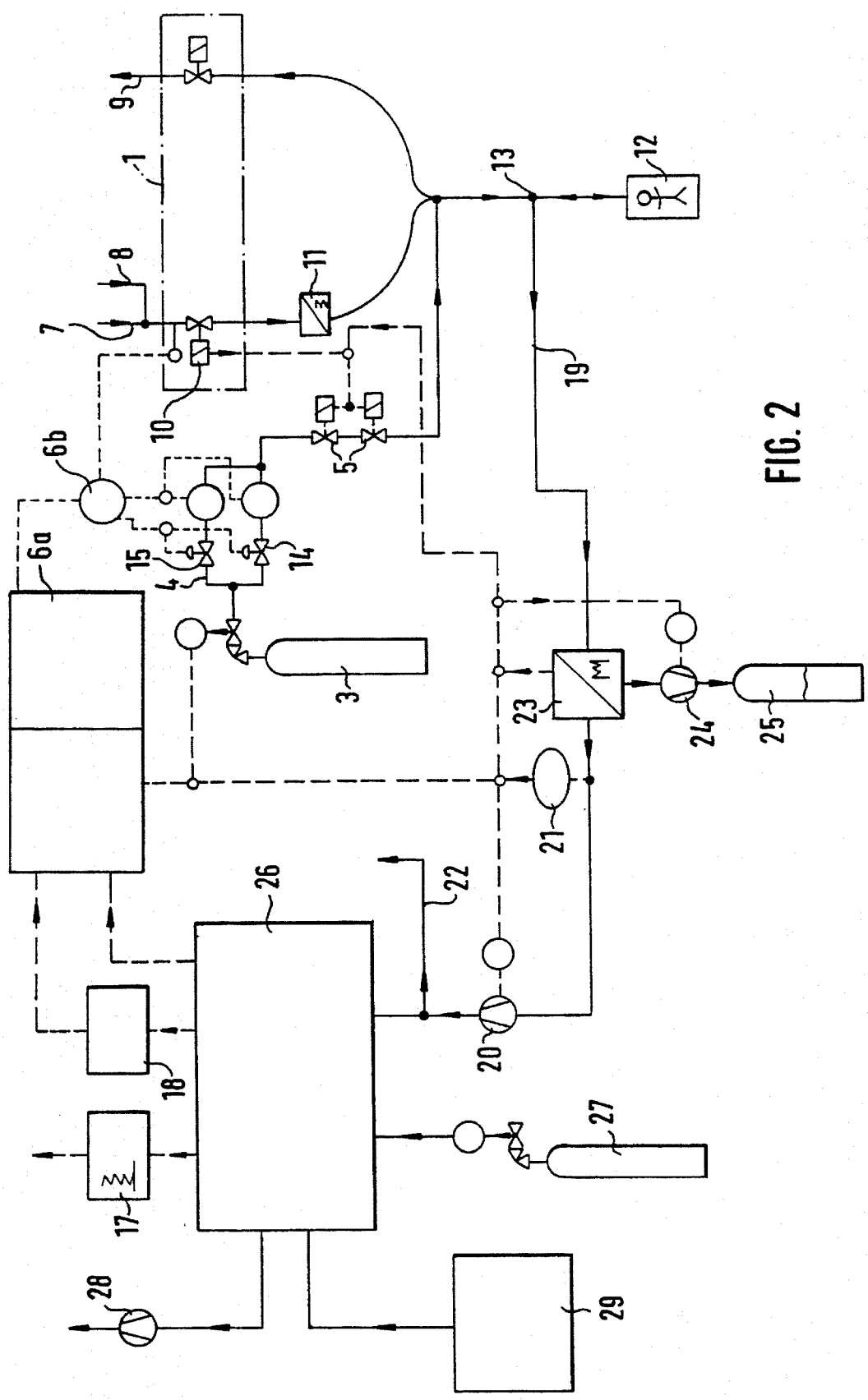
FIG. 2 shows an apparatus which has a chemiluminescence detector as analyzer and which permits the concentrations of NO and $NO_2$ to be established simultaneously.

Patients with ARDS or similar disorders often need to be treated with NO for periods of several weeks. During this treatment period the apparatus ought to operate as fault-free as possible. In order to achieve this, according to another feature of the invention, a dehumidifier 23, preferably a measurement gas condenser, is arranged in the analysis extractor 19. The measurement gas condenser substantially removes the moisture from the analysis gas stream without any reactions of NO and, where appropriate, $NO_2$ taking place. This moisture might lead to side effects, as far as cessation of operation, in the analyzer 2. The moisture removed in the measurement gas condenser is passed by means of the condensate pump 24 into the condensate collecting bottle 25 and removed from time to time. In the apparatus depicted in FIG. 2, the analyzer is designed as chemiluminescence detector 26 which makes it possible to measure the concentrations of NO and $NO_2$ simultaneously. The metering container 3 is a gas cylinder and contains 900 vpm NO in $N_2$. The toxic $NO_2$ is produced in the lungs of the patient 12. There is analysis of the metered-in NO and $NO_2$ contents during the inspiratory phase (inhalation) and of the exhaled gas mixture during the expiratory phase (exhalation). This arrangement therefore makes it possible to interpret the analysis product further and, in particular, interpret the NO uptake and $NO_2$ produced correspondingly. Besides other factors, the amount of NO fed into the tube 13 from the NO metering container 3 determines the amount of $NO_2$ formed. In the chemiluminescence detector 26, NO reacts with ozone which is generated by the chemiluminescence detector 26 itself. This reaction produces light whose intensity is representative of the NO concentration. A test gas is necessary for operating the chemiluminescence detector 26 and is located in the test gas cylinder 27. It comprises 90 vpm NO in nitrogen and is used for checking and calibrating the chemiluminescence detector 26. A vacuum pump 28 and a dry air generator 29 are also necessary for operating the chemiluminescence detector 26. The concentrations of NO and $NO_2$ measured in the chemiluminescence detector 26 are continuously recorded by the recorder 17. The measured concentrations are passed on to the control unit 6a which in turn adjusts, via the metering unit 4 and the control valves 5, the amount of NO supplied to the patient.

The chemiluminescence detector 26 operates with a greatly reduced pressure so that the measurement gas would in fact automatically flow through the analysis extractor 19 to the analyzer 2. The measurement gas pump 20 which is provided according to the invention extracts, in conjunction with the flow monitoring unit 21, from the tube 13 a measurement gas stream which is considerably larger than required for operating the analyzer. In one embodiment of the apparatus, 3 l/min measurement gas are extracted, while the chemiluminescence detector 26 requires only 0.7 l/min. The excess amount of measurement gas is discharged through the bypass line 22. This measure according to the invention results in changes in the concentration of NO and $NO_2$ in the respiratory gas being detected very quickly by the analyzer 2. The NO supply can be adjusted by the control unit 6a and the monitoring and automatic control unit 6b correspondingly quickly.

The rapid change in the NO metering on the basis of the measured concentrations of NO and $NO_2$ has the advantageous result that the minimum amount of toxic $NO_2$ is formed.

I claim:

1. An apparatus for the monitored metering of NO (nitric oxide) into patients' respiratory air, comprising a) a respirator communicating with passageway means for leading to a patient, b) an NO metering container which is connected to said passageway means for supplying NO to the respiratory air supplied to a patient, c) a-metering unit arranged between the respirator and the NO metering container, d) an analyzer connected to said passageway means leading from the respirator to a patient for determining the concentration of NO in a patient's respiratory air, e) a control unit which is connected to the analyzer and acts on the metering unit to control the amount of flow of NO from the NO container to a patient, f) a dehumidifier located in a connecting line between the respirator and the analyzer, and g) a measurement gas pump located in the connecting line between the analyzer and the dehumidifier.

2. An apparatus as claimed in claim 1 wherein the NO metering container is connected to the respiratory arm of the respirator.

3. An apparatus as claimed in claim 2, wherein the dehumidifier is a measurement gas condenser.

4. An apparatus as claimed in claim 3, wherein the analyzer is designed as an apparatus operating on the principle of the measurement of infrared absorption or with electrochemical sensors.

5. An apparatus as claimed in claim 3, wherein the analyzer is designed as a chemiluminescence detector.

6. An apparatus as claimed claim 5, which has an NO limit monitoring unit which is connected to the analyzer and acts on the control unit.

7. An apparatus as claimed in claim 6, which has devices for measuring the inspiration volumetric flow of respiratory air and oxygen, the NO volumetric flow, and a monitoring and automatic control unit in which the measured NO volumetric flow and the analyzed value is fed back as controlled variable for adjusting the amount of NO metered in.

8. An apparatus as claimed in claim 1, wherein the dehumidifier is a measurement gas condenser.

9. An apparatus as claimed in claim 8, wherein the analyzer is designed as an apparatus operating on the principle of the measurement of infrared absorption or with electrochemical sensors.

10. An apparatus as claimed in claim 8, wherein the analyzer is designed as a chemiluminescence detector.

11. An apparatus as claimed in claim 8, which has an NO limit monitoring unit which is connected to the analyzer and acts on the control unit.

12. An apparatus as claimed in claim 8, which has devices for measuring the inspiration volumetric flow of respiratory air and oxygen, the NO volumetric flow, and a monitoring and automatic control unit in which the measured NO volumetric flow and the analyzed value is fed back as controlled variable for adjusting the amount of NO metered in.

13. An apparatus as claimed in claim 1, wherein the analyzer is designed as an apparatus operating on the principle of the measurement of infrared absorption or with electrochemical sensors.

14. An apparatus as claimed in claim 13, which has an NO limit monitoring unit which is connected to the analyzer and acts on the control unit.

15. An apparatus as claimed in claim 13, which has devices for measuring the inspiration volumetric flow of respiratory air and oxygen, the NO volumetric flow, and a monitoring and automatic control unit in which the measured NO volumetric flow and the analyzed value is fed back as controlled variable for adjusting the amount of NO metered in.

16. An apparatus as claimed in claim 1, wherein the analyzer is designed as a chemiluminescence detector.

17. An apparatus as claimed in claim 16, which has an NO limit monitoring unit which is connected to the analyzer and acts on the control unit.

18. An apparatus as claimed in claim 16, which has devices for measuring the inspiration volumetric flow of respiratory air and oxygen, the NO volumetric flow, and a monitoring and automatic control unit in which the measured NO volumetric flow and the analyzed value is fed back as controlled variable for adjusting the amount of NO metered in.

19. An apparatus as claimed in claim 1, which has an NO limit monitoring unit which is connected to the analyzer and acts on the control unit.

20. An apparatus as claimed in claim 1, which has devices for measuring the inspiration volumetric flow of respiratory air and oxygen, the NO volumetric flow, and a monitoring and automatic control unit in which the measured NO volumetric flow and the analyzed value is fed back as controlled variable for adjusting the amount of NO metered in.

21. An apparatus as claimed in claim 1, wherein the analyzer analyzes the amount of NO being exhaled by a patient.

22. An apparatus as claimed in claim 21, wherein the analyzer also analyzes the amount of NO being inhaled by a patient.

23. An apparatus as claimed in claim 22, wherein the analyzer analyzes the amount of $NO_2$ (nitrogen dioxide) being exhaled by a patient.

24. An apparatus as claimed in claim 23, wherein the metering unit stops the flow of NO to the respirator when the amount of NO in the respiratory gas exceeds a predetermined level.

25. An apparatus as claimed in claim 21, wherein the analyzer analyzes the amount of $NO_2$ (nitrogen dioxide) being exhaled by a patient.

26. An apparatus as claimed in claim 1, wherein the metering unit stops the flow of NO to the respirator when the amount of NO in the respiratory gas exceeds a predetermined level.

\* \* \* \* \*